US009393270B2

(12) United States Patent
Morreale

(10) Patent No.: US 9,393,270 B2
(45) Date of Patent: Jul. 19, 2016

(54) METHOD OF PREPARING A BONE GRAFT

(71) Applicant: Vittorio M. Morreale, Rochester, MI (US)

(72) Inventor: Vittorio M. Morreale, Rochester, MI (US)

(*) Notice: Subject to any disclaimer, the term of this patent is extended or adjusted under 35 U.S.C. 154(b) by 0 days.

(21) Appl. No.: 14/803,559

(22) Filed: Jul. 20, 2015

(65) Prior Publication Data

US 2015/0335791 A1     Nov. 26, 2015

Related U.S. Application Data

(63) Continuation-in-part of application No. 13/633,177, filed on Oct. 2, 2012, now abandoned.

(51) Int. Cl.

| | | |
|---|---|---|
| A61L 27/38 | (2006.01) |
| A61K 35/32 | (2015.01) |
| A61F 2/28 | (2006.01) |
| A61L 27/58 | (2006.01) |
| A61L 28/00 | (2006.01) |
| A61L 27/36 | (2006.01) |
| A61L 27/54 | (2006.01) |
| A61K 38/18 | (2006.01) |
| A61L 27/56 | (2006.01) |
| A61K 35/28 | (2015.01) |

(52) U.S. Cl.
CPC . *A61K 35/32* (2013.01); *A61F 2/28* (2013.01); *A61K 35/28* (2013.01); *A61K 38/18* (2013.01); *A61L 27/365* (2013.01); *A61L 27/3608* (2013.01); *A61L 27/3834* (2013.01); *A61L 27/3847* (2013.01); *A61L 27/54* (2013.01); *A61L 27/56* (2013.01); *A61L 27/58* (2013.01); *A61L 28/008* (2013.01); *A61F 2002/2817* (2013.01); *A61L 2300/30* (2013.01); *A61L 2300/414* (2013.01); *A61L 2430/02* (2013.01); *Y10T 137/85986* (2015.04)

(58) Field of Classification Search
CPC .... A61L 27/3847; A61L 27/58; A61L 28/008
See application file for complete search history.

(56) References Cited

U.S. PATENT DOCUMENTS 6,586,388 B2 * 7/2003 Oppermann ........... C07K 14/51
514/16.7

* cited by examiner

*Primary Examiner* — Carlos Azpuru
(74) *Attorney, Agent, or Firm* — Quinn Law Group, PLLC

(57) ABSTRACT

A vacuum container supports a macroscopic sized cancellous device fully immersed within a solution of a bone growth promoting substance in a sealed chamber. The solution may include one of a Demineralized Bone Matrix (DBM) solution, a morphegenic protein solution, or a stem cell solution. A vacuum creating device is in fluid communication with the sealed chamber, and is operable to remove air from within the sealed chamber to create a vacuum therein. Removing air from the sealed chamber also removes air from a plurality of voids in the cancellous device, which allows the solution to fill the voids and saturate the cancellous device in preparation for use as a bone graft. The cancellous device may further be agitated while the air is being removed from the voids in the cancellous device to further promote saturation of the voids in the cancellous device with the solution.

12 Claims, 3 Drawing Sheets

METHOD OF PREPARING A BONE GRAFT

CROSS-REFERENCE TO RELATED APPLICATIONS

This application is a Continuation In Part application of U.S. patent application Ser. No. 13/633,177, filed on Oct. 2, 2012.

TECHNICAL FIELD

The invention generally relates to a method for preparing a cancellous device for use as a bone graft.

BACKGROUND

Bone grafting is a surgical procedure that places new bone or a replacement material into spaces between or around broken bone (fractures) or in holes in bone (defects) to aid in healing. Bone grafting is used to repair bone fractures that are extremely complex, pose a significant risk to the patient, or fail to heal properly. Bone grafting is also used to help fusion between vertebrae, correct deformities, or provide structural support for fractures of the spine. In addition to fracture repair, bone grafting is used to repair defects in bone caused by congenital disorders, traumatic injury, or surgery for bone cancer. Bone grafts are also used for facial or cranial reconstruction.

The term "graft" commonly refers to an autograft or allograft. A graft made of bone from the patient's own body (e.g., hip bones or ribs) is an autograft. An allograft uses bone from a cadaver, which has been frozen and stored in a tissue bank. Synthetic bone material may also be used as a graft. To place a bone graft, a surgeon makes an incision in the skin over the bone defect, and shapes the bone graft or replacement material to fit into it. After the graft is placed into the defect, it is held in place with pins, plates, or screws.

In surgery of the spine, especially spinal fusion (also called arthrodesis), surgeons may decide to use bone grafts to assist in the healing and remodeling of the spine after surgery. Normally, small pieces of bone are placed into the space between the vertebrae to be fused, and sometimes larger solid pieces of bone provide immediate structural support. Spinal fusion involves the surgical treatment of abnormalities in the vertebrae, such as curvatures, scoliosis or kyphosis, or injuries (fractures). For example, cervical spinal fusion joins selected bones in the neck. Bone grafts may be used for many different procedures, including but not limited to spinal fusion surgery, orthopedics, podiatry, dentistry, etc.

Demineralized Bone Matrix (DBM) is allograft bone that has had the inorganic mineral removed, leaving behind the organic collagen matrix. Removal of the bone mineral exposes more biologically active bone morphogenetic proteins. These growth factors modulate the differentiation of progenitor cells into osteoprogenitor cells, which are responsible for bone and cartilage formation, thereby promoting bone growth. Bone tissue is a porous, matrix-like structure. The success of a bone graft is determined by its ability to recruit host cells to the site of the graft and modulate their conversion into bone forming cells.

SUMMARY

A method of performing a bone graft surgery is provided. The method includes immersing a cancellous device within a solution of bone growth promoting material, in a sealed chamber of a container. The cancellous device defines a plurality of voids, and includes a macroscopic size. The cancellous device may include a porosity approximately equivalent to that of cancellous bone, having a porosity of 75-85% and an average pore size or dimension of between 300-600 μm. The average pore size may include any dimension, e.g., width, of the pore, that is measured along a straight line between opposing sides or surfaces of the void. Alternatively, the cancellous device may include a porosity approximately equivalent to that of cortical bone, having a porosity of 5-10% and an average pore size or dimension of between 10-50 μm. A vacuum is applied to the sealed chamber of the container to remove air from the plurality of voids in the cancellous device, while the cancellous device is immersed in the solution of bone growth promoting material. While the cancellous device is immersed in the solution of bone growth promoting material and the vacuum is being applied to the sealed chamber, the cancellous device is then agitated to displace the air within the plurality of voids and allow the solution of bone growth promoting material to fill the voids and saturate the cancellous device. Once the voids of the cancellous device are saturated with the solution of bone growth promoting material, the cancellous device is attached to a bone of a patient.

Accordingly, the cancellous device is fully saturated with the solution, which may include but is not limited to a solution of DBM, in preparation for use as a bone graft. The solution promotes bone growth. Therefore, by saturating the cancellous device with the solution, bone growth adjacent the bone graft is improved. The vacuum container removes the air from the voids of the cancellous device, thereby allowing the solution to fill the voids and saturate the cancellous device.

The above features and advantages and other features and advantages of the present invention are readily apparent from the following detailed description of the best modes for carrying out the invention when taken in connection with the accompanying drawings.

DETAILED DESCRIPTION

Those having ordinary skill in the art will recognize that terms such as "above," "below," "upward," "downward," "top," "bottom," etc., are used descriptively for the figures, and do not represent limitations on the scope of the invention, as defined by the appended claims.

Referring to the Figures, wherein like numerals indicate like parts throughout the several views, a vacuum container is generally shown at 20. The vacuum container 20 is configured for saturating a cancellous device 22 with a solution for use as a bone graft. The solution includes a bone growth promoting substance, such as but not limited to Demineralized Bone Matrix (DBM), morphogenic proteins, stem cells, saline, or antibiotics. The solution is prepared as a liquid. While the written description below describes the solution as a solution of DBM, it should be appreciated that the solution may be comprised of one or more substances other than the DBM. Accordingly, the solution is not limited to a solution of DBM. As used herein, the term Demineralized Bone Matrix (DBM) is defined as an allograft or autograft bone material having all inorganic bone minerals removed, leaving only the organic collagen bone matrix. The DBM includes growth properties that promote bone growth within the human body.

Figure 3:
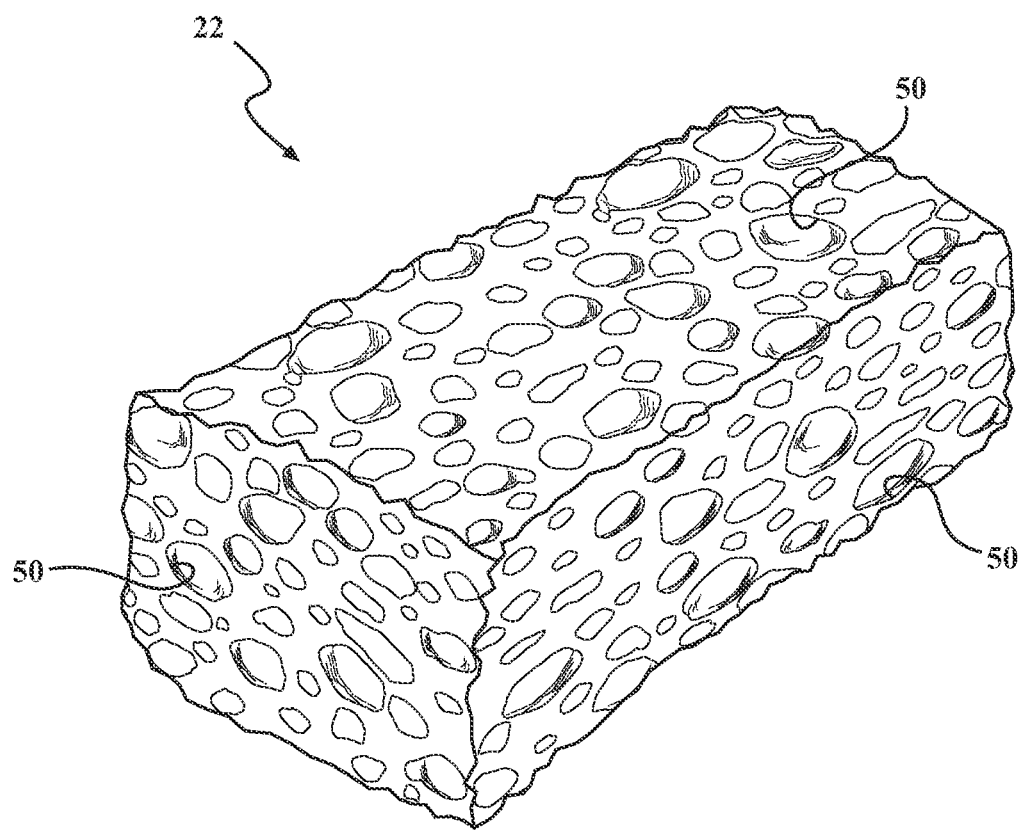
FIG. 3 is a schematic perspective view of a cancellous device used for a bone graft.

As used herein, the term "cancellous" is defined as having a spongy or porous internal structure defining a plurality of voids. The cancellous device 22 may include a patient's own bone material, cadaveric bone material, a synthetic bone material, or some other porous material suitable for use as a bone graft. Referring to FIG. 3, the cancellous device 22 is a macroscopically sized object, having dimensions that may range between 1 mm and 15 mm. The cancellous device includes an exterior surface that defines a volume of the cancellous device 22. The volume of the cancellous device is equal to or greater than 8.0 mm$^3$. As noted above, the cancellous device 22 includes a plurality of internal voids 50, defined by the structure of the cancellous device 22. At least one of the voids 50 defines a dimension that is greater than 10 μm.

Figure 1:
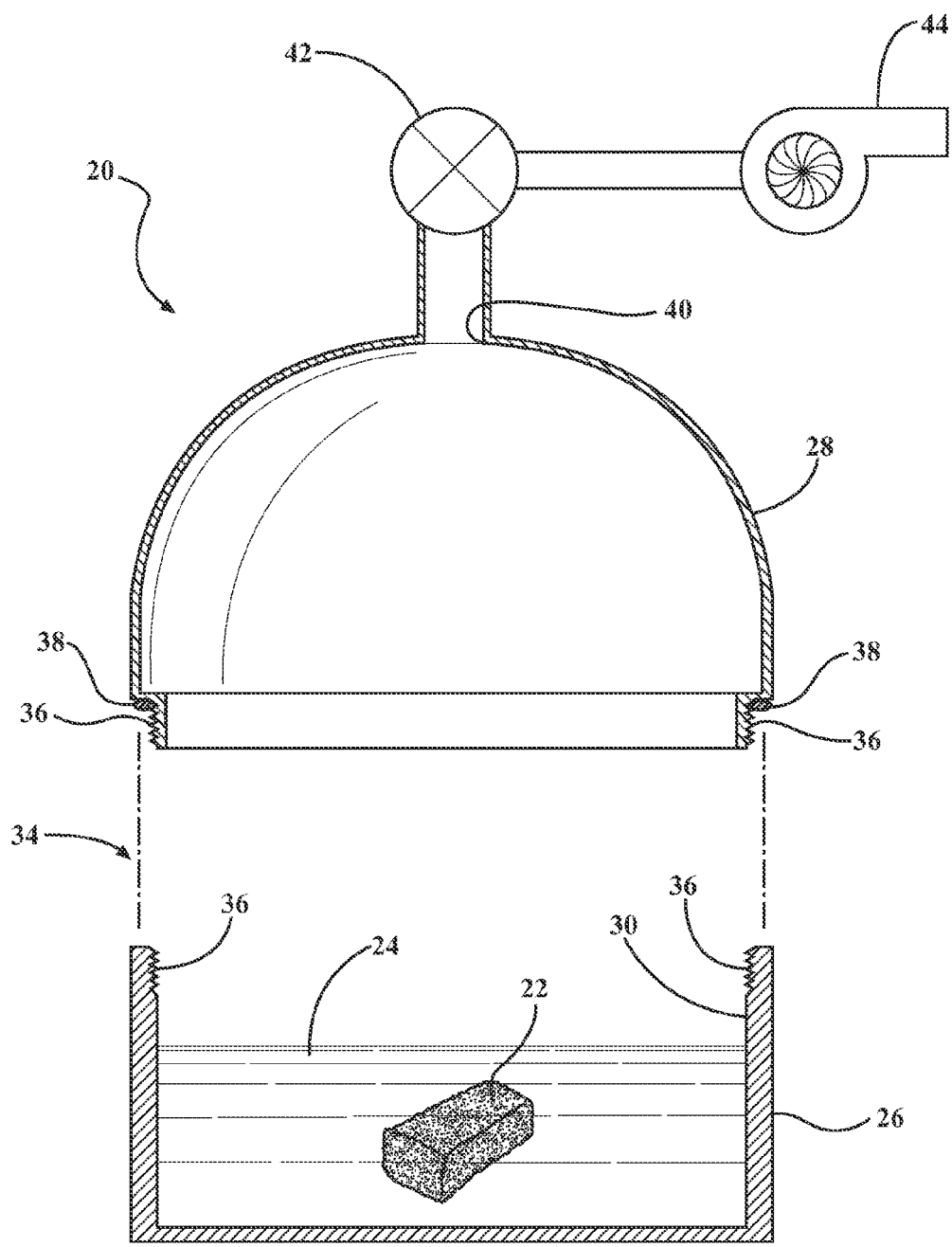
FIG. 1 is a schematic cross sectional view of a vacuum container for saturating a cancellous device with a solution of Demineralized Bone Matrix (DBM) for use as a bone graft, showing an upper portion of the vacuum container detached from a lower portion of the vacuum container.
Figure 2:
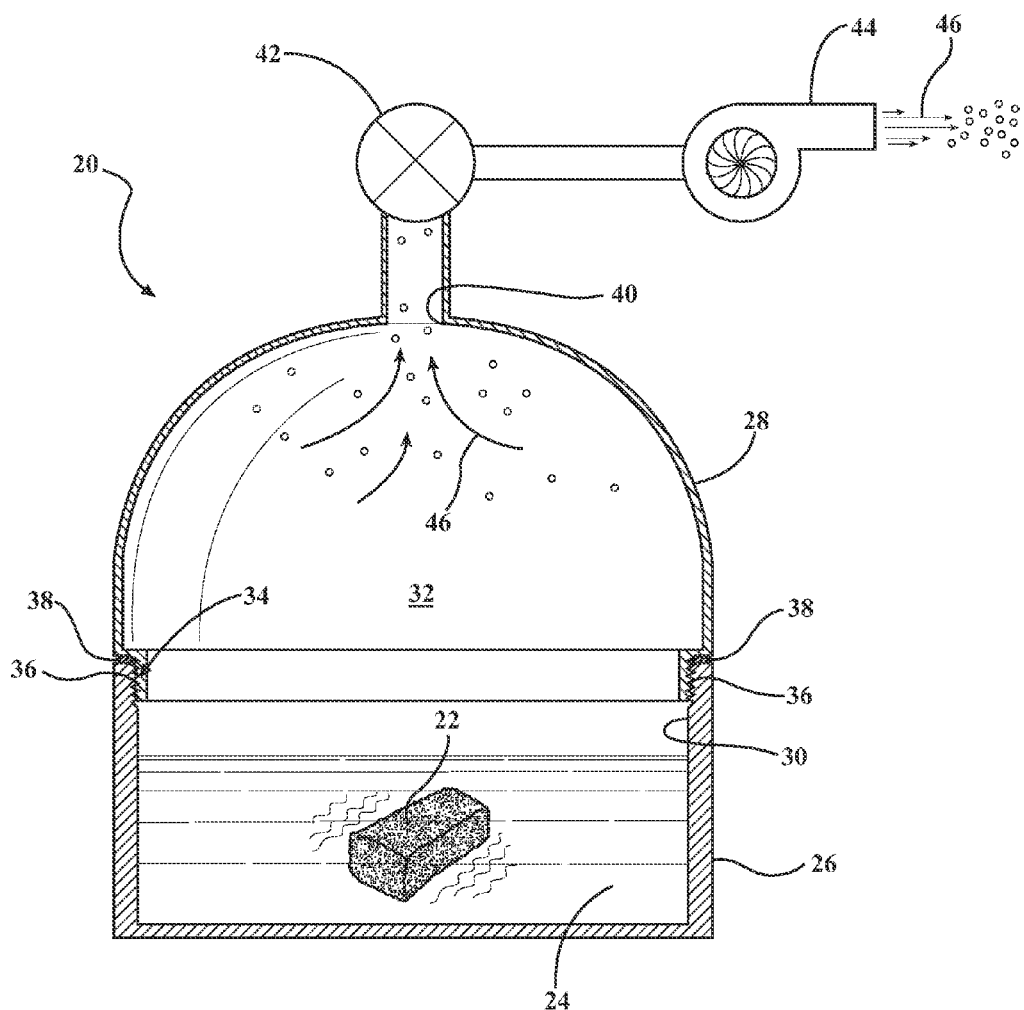
FIG. 2 is a schematic cross sectional view of the vacuum container showing the upper portion attached to the lower portion, and a vacuum creating device removing air from within a sealed chamber of the vacuum container.

Referring to FIGS. 1 and 2, the vacuum container 20 includes a lower portion 26 and an upper portion 28. The lower portion 26 defines a reservoir 30 that is sized and shaped to contain the cancellous device 22 fully immersed within the solution of DBM 24. The upper portion 28 is removably attached to the lower portion 26. As shown in FIG. 1, the upper portion 28 is removable from the lower portion 26 to expose the reservoir 30 of the lower portion 26 to allow placement of the cancellous device 22 and the solution of DBM 24. When attached to the lower portion 26, as shown in FIG. 2, the upper portion 28 is disposed in sealing engagement with the lower portion 26 to define a sealed chamber 32 therebetween.

The vacuum container 20 includes an attachment mechanism 34 that interconnects the lower portion 26 and the upper portion 28. The attachment mechanism 34 may include any suitable device capable of securely attaching the upper portion 28 and the lower portion 26. For example, the attachment mechanism 34 may include threads 36 formed into both the upper portion 28 and the lower portion 26 and defining a threaded connection interconnecting the lower portion 26 and the upper portion 28 in threaded engagement. Alternatively, the attachment mechanism 34 may include one or more clamps (not shown) disposed about the periphery of the vacuum container 20 and configured for clamping the upper portion 28 and the lower portion 26 together. It should be appreciated that the attachment mechanism 34 may include some other device and/or configuration incorporated into the upper portion 28 and/or the lower portion 26 not described herein nor shown in the drawings that is capable of attaching the upper portion 28 and the lower portion 26.

The vacuum container 20 further includes a seal 38 disposed between the lower portion 26 and the upper portion 28 for sealing therebetween. The seal 38 may be attached to either the upper portion 28 or the lower portion 26, and seals between the upper portion 28 and the lower portion 26 to prevent the infiltration and exfiltration of fluids and/or gases into the sealed chamber 32 of the container when the upper portion 28 is attached to the lower portion 26. The seal 38 may include any suitable device, such as but not limited to an elastomeric o-ring, gasket, or other similar device.

The upper portion 28 of the vacuum container 20 defines an opening 40 extending therethrough into the sealed chamber 32. Preferably, and as shown, the opening 40 is defined by an upper wall of the upper portion 28. However, it should be appreciated that the opening 40 may be disposed on a side wall of the upper portion 28. A valve 42 is coupled to the upper portion 28 and disposed in fluid communication with the opening 40. The valve 42 is operable to open and close fluid communication through the opening 40. Accordingly, the valve 42 is moveable between an open position allowing fluid communication through the opening 40, and a closed position blocking fluid communication through the opening 40 and sealing the sealed chamber 32.

A vacuum creating device 44 is coupled to the valve 42 and disposed in fluid communication with the valve 42. The vacuum creating device 44 is operable to remove air from within the sealed chamber 32 to create a vacuum within the sealed chamber 32. The vacuum creating device 44 should be capable of creating a vacuum having a gauge pressure of at least equal to or less than −10 psi. Accordingly, the vacuum is at least −10 psi. As such, with the valve 42 disposed in the open position, the vacuum creating device 44 may be operated to remove the air from within the sealed chamber 32, generally represented by the flow arrow 46 shown in FIG. 2, after which, the valve 42 may be moved into the closed position to close the opening 40 and seal 38 the sealed chamber 32, thereby maintaining the vacuum in the sealed chamber 32. The vacuum creating device 44 may include, but is not limited to, a syringe or a vacuum pump. It should be appreciated that the vacuum creating device 44 may include some other device capable of removing the air from within the sealed chamber 32.

A method of preparing the bone graft, and a method of performing a grafting operation with the prepared bone graft are also provided. The cancellous device 22 is prepared for use as a bone graft by preparing the solution of bone growth promoting material, such as the solution of DBM 24. The solution of DBM 24 may be prepared in any manner suitable for sue with a bone graft, and is dependent on the specific substance and form of the bone growth promoting material used. For example, the solution may be prepared by suspending stem cells in amniotic fluid.

Once the solution of DBM 24 is prepared, the cancellous device 22 and the solution of DBM 24 are placed within the reservoir 30 of the lower portion 26, and the cancellous device 22 is fully submerged within and surrounded by the solution of DBM 24. When the cancellous device 22 is fully immersed within the solution of DBM 24, the upper portion 28 of the vacuum container 20 is attached to the lower portion 26 of the vacuum container 20 to define the sealed chamber 32 therebetween.

Once the upper portion 28 is attached to the lower portion 26, the valve 42 is opened, and the vacuum creating device 44 is engaged to remove the air from within the sealed chamber 32 through the opening 40 in the upper portion 28, thereby creating a vacuum therein. It should be appreciated that the vacuum creating device 44 must operate for a time period sufficient form a vacuum (gauge pressure) of at least −10 psi in order to draw the air out of the voids of the cancellous device 22, and through the solution of DBM 24. For example, the vacuum may need to be applied for a period of 30 seconds. However, the vacuum may be applied for longer periods if necessary, such as for example, 2 minutes. It should be appreciated that the vacuum may be applied for longer periods if so desired.

Once the cancellous device 22 is immersed with in the solution of DBM 24, and while the vacuum is being applied to the sealed chamber, the cancellous device 22 may be agitated, e.g., shaken. The cancellous device 22 may be agitated in any suitable manner, such as by shaking the vacuum container 20 by hand, or attaching the vacuum container 20 to a vibrating base (not shown) to shake the vacuum container 20 and thereby agitate or shake the cancellous device 22 within the solution of DBM 24.

Surface tension between the cancellous device 22 and the solution of DBM 24 inhibits the ability of the solution of DBM 24 to penetrate the voids of the cancellous device 22. The applied vacuum helps to draw out the air from within the voids of the cancellous device, thereby allowing the solution of the DBM 24 to flow into and fill the voids. By removing the air from within the sealed chamber 32 and forming the vacuum therein, the air from the plurality of voids in the cancellous device 22 is also removed. Removing the air from the voids in the cancellous device 22, while the cancellous device 22 is immersed in the solution of DBM 24, allows the solution to fill the voids and fully saturate the cancellous device 22. Agitating the cancellous device 22 in the solution of DBM 24 while the cancellous device 22 is immersed in the solution of DBM 24 and under the vacuum, increases the effectiveness of the vacuum in removing the air from the voids of the cancellous device 22, thereby improving the saturation of the voids of the cancellous device, until the cancellous device 22 is completely rehydrated and saturated. The applied vacuum and agitation of the cancellous device 22 helps overcome the surface tension between the solution of DBM 24 and the cancellous device 22, drawing the air within the voids of the cancellous device out and and also drawing the solution of DBM 24 into the voids to replace the removed air.

Once the air is removed from the sealed chamber 32 and the vacuum is formed to the proper pressure range, the valve 42 may be closed to seal 38 the opening 40 to maintain the vacuum in the sealed chamber 32. The vacuum in the sealed chamber 32 may be maintained for a time period sufficient to allow the solution of DBM 24 to fully saturate the cancellous device 22. As noted above, the vacuum may be maintained for any time period, but a period of approximately 30 seconds should be sufficient for most procedures. It should be appreciated that the time period required to allow the solution of DBM 24 to infiltrate into the voids of the cancellous device 22 may depend upon the size and consistency of the cancellous device 22, and upon the properties of the solution of DBM 24. Once adequate time has passed to fully saturate the cancellous device 22, the valve 42 may be opened to release the vacuum within the sealed chamber 32, thereby allowing the upper portion 28 to be removed from the lower portion 26, and the saturated cancellous device 22 to be removed from the reservoir 30 and used as a bone graft.

While the method is described above using the vacuum container 20 shown in the Figures, it should be appreciated that the method may be practiced with any container capable of supporting the cancellous device 22 in a solution of bone growth promoting material, and forming a vacuum therein, such as but not limited to a specially configured syringe. Accordingly the method described and claimed herein is not limited to use with the vacuum container 20 described and claimed herein.

Once the voids of the cancellous device 22 have been saturated with the solution of DBM 24 and removed from the vacuum container 20, the cancellous device may be attached to a bone of a patient as a bone graft. The cancellous device 22 may be attached in any suitable manner. For example, the cancellous device 22 may be attached with one or more mechanical fasteners, such as screws or the like. The manner and/or procedure of the surgery in which the cancellous device 22 is attached to the bone may vary depending upon the specific type and/or location of the bone graft, is not pertinent to the teachings of this disclosure, and are therefore not described in detail herein.

The method described above disburses the osteogenic signal completely throughout the cancellous device 22, including the center of the cancellous device 22, which helps to promote osteogenesis throughout the entire bone graft, thereby encouraging early and complete graft incorporation. Allograft material can sometimes be inconsistent from one piece of allograft to another. Saturation, complete rehydration and complete disbursement of the DBM solution 24 throughout the allograft material, i.e., the cancellous device 22, ensures consistency of the overall product from graft to graft and patient to patient. The above described process provides consistent results from one piece of allograft to the next, and provides for reproducible results.

EXAMPLE

A retrospective analysis was performed on the surgical outcomes of 100 patients who underwent anterior cervical fusion surgery with unicortical dense cancellous human allograft tissue combined with a solution consisting of saline and dissolved demineralized bone matrix used as the bone graft. In half of the patients the graft was placed in the solution to soak and the other half of patients the graft and solution were subjected to a vacuum technique in order fully saturate the graft with solution.

The retrospective analysis was performed to assess the effectiveness of using vacuum assistance to saturate dense cancellous bone graft implants with a solution of demineralized bone matrix (DBM) for use in anterior cervical fusion (ACF) surgery. Two groups of patients were studied. In each group there were fifty patients. In the first group, Group A, unicortical dense cancellous bone grafts were prepared by placing the bone graft in a solution which consisted of 5 cc of sterile saline solution with 1 cc of DBM and letting the graft soak for approximately 5 minutes. In the second group, Group B, the bone grafts were placed in a device containing the same DBM solution as in Group A. Then the device was sealed and a vacuum was created for 30 seconds causing the air to be displaced from the bone graft and be replaced by DBM solution thereby completely saturating the bone graft. For both Group A and Group B, 50 consecutive surgeries were chosen for each group. The unicortical dense cancellous bone grafts and the DBM were obtained from the same source for all 100 patients. The patient demographics are summarized in Table 1.

TABLE 1

| | Group A | Group B |
|---|---|---|
| Number of Patients | 50 | 50 |
| Females | 28 | 23 |
| Males | 22 | 27 |
| Ages | 21-72 | 27-76 |
| Levels fused: | | |
| 1 level | 38 | 38 |
| 2 levels | 7 | 6 |
| 3 levels | 5 | 6 |
| Total number of levels | 67 | 68 |
| Bone graft heights | 8 mm-11 mm | 8 mm-11 mm |
| Number of smokers | 10 | 9 |

A successful outcome was defined by satisfactory fusion at every level operated. An unsuccessful outcome was defined by a nonunion at any level. Satisfactory fusion was defined by evidence of incorporation of the graft, no evidence of lucency within the disk space either at the graft-endplate interface or within the graft itself, no movement between adjacent levels on flexion and extension x-ray and no evidence of loosening of hardware. Unsatisfactory fusion (nonunion) consisted of any evidence of nonunion including lucency within the disk space confirmed with CT, loosening of hardware or movement on flexion and extension x-rays.

In Group A there were a total of 62 out of 67 (93%) successfully fused levels. In Group B there were 67 out of 68 levels (99%) that successfully fused. In Group A 3 1-level ACFs did not fuse, 1 segment in 1 2-level ACF did not fuse and 1 segment in 1 3-level ACF did not fuse. Only 1 patient required return to surgery for a symptomatic nonunion. In Group B the 1 nonunion was asymptomatic and did not require return to surgery. Of the 5 patients who had a nonunion in Group A 4 were smokers. The 1 patient who had a nonunion in Group B was not a smoker. The results are summarized in Table 2.

TABLE 2

|  | Group A | Group B |
| --- | --- | --- |
| Successful outcomes | 45 | 49 |
| Unsuccessful outcomes | 5 | 1 |
| Successful levels | 62 | 67 |
| Unsuccessful levels | 5 | 1 |
| 1 level | 3 | 1 |
| 2 levels | 1 | 0 |
| 3 levels | 1 | 0 |
| Smokers | 4 | 0 |
| Symptomatic nonunion | 1 | 0 |
| Reoperation | 1 | 0 |

In this retrospective analysis, the use of vacuum assistance to replace the air in dense cancellous bone graft appeared to be beneficial in increasing the fusion rate among patients undergoing anterior cervical fusion.

The detailed description and the drawings or figures are supportive and descriptive of the invention, but the scope of the invention is defined solely by the claims. While some of the best modes and other embodiments for carrying out the claimed invention have been described in detail, various alternative designs and embodiments exist for practicing the invention defined in the appended claims.

The invention claimed is:

1. A method of performing a bone graft, the method comprising:
    immersing a porous device defining a plurality of voids within a solution of bone growth promoting material in a sealed container, wherein the porous device includes a macroscopic size with at least one of the voids of the porous device having a dimension greater than 10 μm, with the macroscopic size of the porous device defined as a device having a volume equal to or greater than 8.0 mm$^3$;
    applying a vacuum to the sealed container to remove air from the plurality of voids in the porous device, while the porous device is immersed in the solution of bone growth promoting material;
    agitating the porous device, while the porous device is immersed in the solution of bone growth promoting material and the vacuum is being applied to the sealed chamber, to displace the air within the plurality of voids and allow the solution of bone growth promoting material to fill the voids and saturate the porous device; and
    attaching the porous device to a bone.

2. The method as set forth in claim 1 wherein the solution of bone growth promoting material includes one of a Demineralized Bone Matrix (DBM) solution, a morphogenic protein solution, a stem cell solution, saline, or antibiotics.

3. The method as set forth in claim 2 further comprising preparing the solution of DBM.

4. The method as set forth in claim 1 wherein immersing the porous device within the solution is further defined as immersing the porous device within the solution such that the porous device is completely submerged and surrounded by the solution.

5. The method as set forth in claim 1 wherein the porous device includes cadaveric bone.

6. The method set forth in claim 1 wherein the applied vacuum includes a gauge pressure equal to or less than −10 psi.

7. The method set forth in claim 1 wherein attaching the porous device to a bone is further defined as attaching the porous device to the bone with at least on mechanical fastener.

8. A method of preparing a porous device for use as a bone graft, wherein the porous device includes a macroscopic size defining a volume equal to or greater than 8.0 mm$^3$, and wherein the porous device includes a plurality of voids, with at least one of the voids of the porous device having a dimension greater than 10 μm, the method comprising:
    immersing the porous device within a solution of bone growth promoting material in a sealed container;
    applying a vacuum to the sealed container to remove air from the plurality of voids in the porous device, while the porous device is immersed in the solution of bone growth promoting material, wherein the applied vacuum includes a gauge pressure equal to or less than −10 psi; and
    agitating the porous device, while the porous device is immersed in the solution of bone growth promoting material and the vacuum is being applied to the sealed chamber, to displace the air within the plurality of voids and allow the solution of bone growth promoting material to fill the voids and saturate the porous device.

9. The method as set forth in claim 8 wherein the solution of bone growth promoting material includes one of a Demineralized Bone Matrix (DBM) solution, a morphogenic protein solution, or a stem cell solution.

10. The method as set forth in claim 9 further comprising preparing the solution of DBM.

11. The method as set forth in claim 8 wherein immersing the porous device within the solution is further defined as immersing the porous device within the solution such that the porous device is completely submerged and surrounded by the solution.

12. The method set forth in claim 8 wherein applying the vacuum to the sealed container to remove air from the plurality of voids in the porous device is further defined as applying the vacuum for a period of time equal to or less than 2 minutes.

* * * * *